United States Patent [19]

Blount

[11] Patent Number: 4,785,802

[45] Date of Patent: Nov. 22, 1988

[54] PROSTHESIS

[76] Inventor: Luther H. Blount, 1 Shipyard La., Warren, R.I. 02885

[21] Appl. No.: 79,873

[22] Filed: Jul. 29, 1987

[51] Int. Cl.$^4$ .............................................. A61F 5/41
[52] U.S. Cl. ..................................................... 128/79
[58] Field of Search ........................................ 128/79

[56] References Cited

U.S. PATENT DOCUMENTS

| | | | |
|---|---|---|---|
| 764,801 | 7/1904 | Emerson | 128/79 |
| 853,410 | 5/1907 | Huebner | 128/79 |
| 4,262,662 | 4/1981 | Allinson | 128/79 |
| 4,262,663 | 4/1981 | Allinson | 128/79 |
| 4,440,183 | 4/1984 | Miller | 128/79 |

FOREIGN PATENT DOCUMENTS

| | | | |
|---|---|---|---|
| 98024 | 9/1924 | Austria | 128/79 |
| 112737 | 4/1929 | Austria | 128/79 |
| 614549 | 6/1935 | Fed. Rep. of Germany | 128/79 |
| 714925 | 12/1941 | Fed. Rep. of Germany | 128/79 |
| 831874 | 2/1952 | Fed. Rep. of Germany | 128/79 |
| 711544 | 9/1931 | France | 128/79 |
| 60397 | 7/1912 | Switzerland | 128/79 |
| 547535 | 9/1942 | United Kingdom | 128/79 |
| 884357 | 12/1961 | United Kingdom | 128/79 |
| 1144083 | 3/1969 | United Kingdom | 128/79 |

Primary Examiner—Gene Mancene
Assistant Examiner—Cary E. Stone
Attorney, Agent, or Firm—Salter & Michaelson

[57] ABSTRACT

A prosthesis for maintaining the male penis in an erected disposition during sexual intercourse includes an open ring-like end portion which is receivable in substantially encircling relation on the shaft of a penis adjacent the base of the glans, a pair of support wire elements which extend rearwardly from the end portion along the underside of the penis and along opposite sides of the scrotum to points therebehind, and a retaining ring slidably received on the support wire elements and positionable thereon adjacent the end portion for closing the end portion around the penis. The prosthesis further includes a resilient band element which is securable to at least one of the support wire elements behind the scrotum and postionable so that it extends over the upper side of the penis adjacent to the base thereof for urging the penis forwardly and also slightly upwardly. The preferred form of the prosthesis further includes a stabilizer member which is attached to the support wire elements behind the scrotum and extends rearwardly and upwardly in the posterior crevice between the buttocks for adding further stability to the prosthesis.

8 Claims, 1 Drawing Sheet

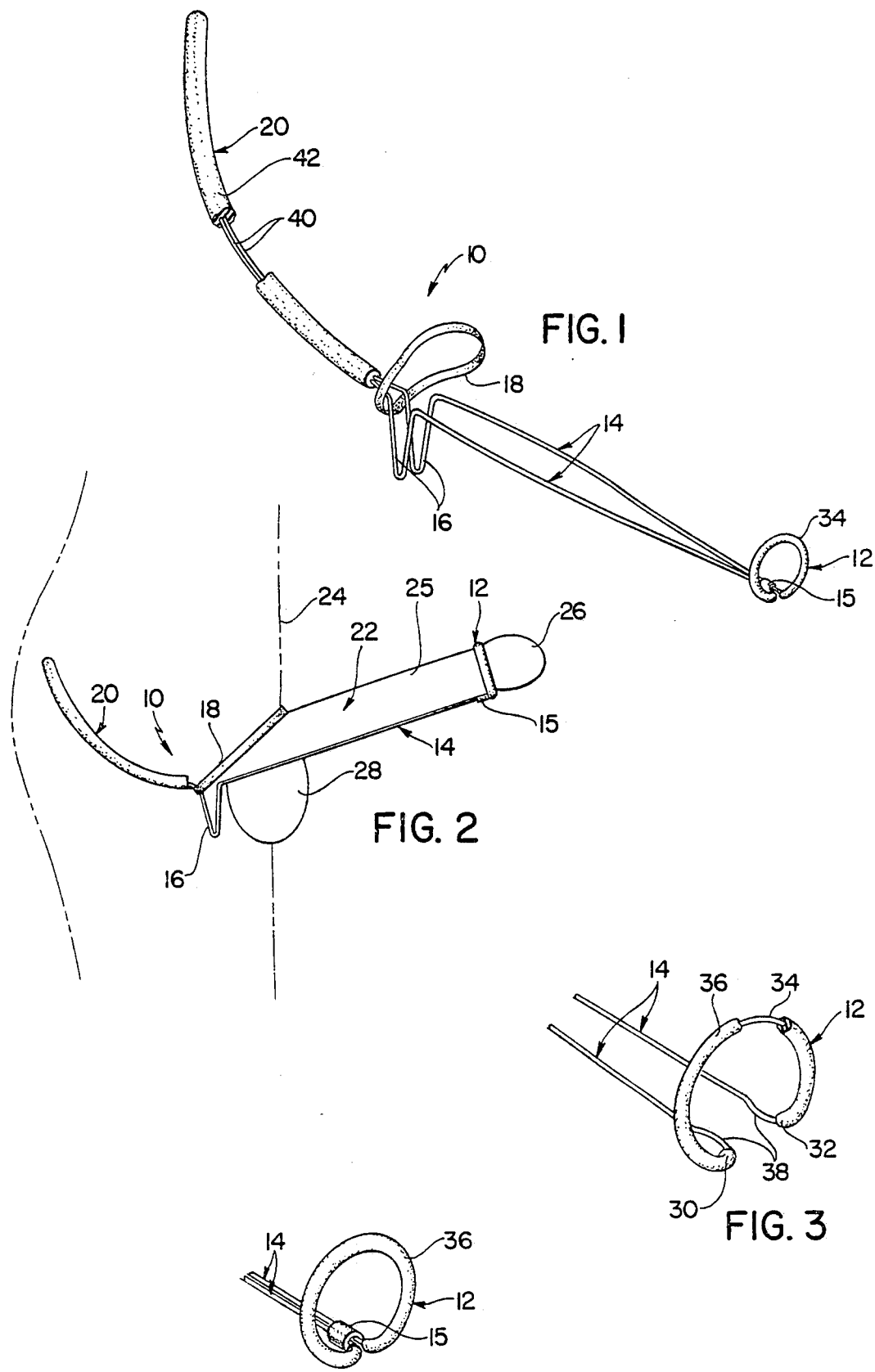

PROSTHESIS

BACKGROUND AND SUMMARY OF THE INVENTION

The instant invention relates to prosthetic devices and more particularly to a prosthesis for maintaining the penis of a human male in an erected disposition during sexual intercourse.

It is generally recognized that sexual fulfillment is an important ingredient in most marriages and other intimate relationships between members of opposite sexes. However, it has been found that a significant number of men suffer from male impotency, which essentially prevents them from participating in sexual conduct. In this regard, it has been further found that while in some cases male impotency which is caused by psychological problems or certain physical problems can be cured, in other cases male impotency which results from surgery or from certain diseases, such as diabetes, is essentially incurable.

A number of devices have been heretofore available for assisting impotent males in performing sexual intercourse. In this regard, the devices disclosed in the U.S. patents to Williams, U.S. Pat. No. 837,993; Renois, U.S. Pat. No. 1,346,463; Bennett, U.S. Pat. No. 1,462,000; Line, U.S. Pat. No. 3,920,007; Allinson, U.S. Pat. No. 4,262,662; Allinson, U.S. Pat. No. 4,262,663; and Gorokhovsky et al, U.S. Pat. No. 4,362,152 are generally exemplary of the heretofore available prosthetic devices of this general type and represent the closest prior art to the subject invention of which the applicant is aware. However, it has generally been found that these devices are not capable of effectively and comfortably maintaining the male penis in a natural erected disposition and that they are not capable of providing natural degrees of stability and rigidity in the male penis. Accordingly, in many instances the devices disclosed in the above references have been found to be less than entirely satisfactory.

The instant invention provides an improved prosthesis which is capable of comfortably maintaining a male penis in an erected deposition with a natural degree of stability and rigidity to enable an impotent male to effectively perform sexual intercourse. Specifically, the prosthesis of the instant invention comprises an open ring-like end portion having opposite first and second ends and dimensioned to be received on the shaft of a male penis so that it extends substantially therearound adjacent the base of the glans of the penis with the first and second ends disposed on the underside of the penis. The prosthesis further comprises a pair of substantially rigid support wire elements which are attached to the first and second ends of the end portion and extend rearwardly along the underside of the penis and along opposite sides of the scrotum to points behind the scrotum when the end portion is assembled on the penis. The prosthesis still further comprises a resilient band and means for securing the band to the wire elements behind the scrotum, the band being adapted so that when it is secured to the wire elements it is receivable on a penis so that it extends across the upper side thereof adjacent the base thereof for resiliently urging the wire elements and the end portion forwardly and slightly upwardly to maintain the penis in a natural erected disposition. The end portion preferably comprises a substantially ring-like wire element which is integrally formed with the support wire elements and a cushioned outer casing over the ring-like wire element for cushioning the penis where the ring-like end portion extends therearound. The securing means for securing the resilient band to the wire elements preferably comprises a pair of downwardly extending wire loops which are integrally formed with the support wire elements behind the scrotum for providing means for releasably hooking the resilient band on the rear ends of the support wire elements to urge the support wire elements forwardly and also slightly upwardly. The prosthesis preferably further comprises a retaining ring which is slidably received on the support wire elements and which is receivable on the support wire elements adjacent the end portion for drawing the first and second ends of the end portion together in order to tighten the end portion around the penis. Still further, the prosthesis preferably comprises a stabilizer member which is connected to the support wire elements so that it extends rearwardly and upwardly in the posterior crevice between the buttocks when the prosthesis is assembled on a male for stabilizing the support wire elements during sexual intercourse. The stabilizer member preferably comprises a pair of stabilizer wire elements which extend integrally rearwardly from the wire loops and a cushioned outer casing on the stabilizer wire elements for cushioning the adjacent portions of the male body during sexual intercourse.

It has been found that the prosthesis of the instant invention can be effectively utilized for supporting the male penis in an erected disposition during sexual intercourse. In this regard, the end portion snugly engages the shaft of the penis adjacent the base of the glans, and the retainer ring is slidably received on the support wire elements for drawing the first and second ends of the end portion together in order to retain the end portion in snug engagement around the penis. The resilient band extends from a point behind the scrotum over the upper side of the penis adjacent the base thereof for urging the support wire elements and the end portion forwardly and also slightly upwardly. The stabilizer member extends rearwardly and upwardly in the posterior crevice between the buttocks for providing stability for the support wire elements during use of the prosthesis. It has been found that these features cooperate to enable the prosthesis to be comfortably and effectively utilized for maintaining the male penis in an erected disposition during sexual intercourse.

As a result, it is a primary object of the instant invention to provide an improved prosthesis for maintaining the male penis in an erected disposition during sexual intercourse.

Another object of the instant invention is to provide a prosthesis which is operative for maintaining the male penis in an erected disposition with a natural degree of rigidity and stability.

Another object of the instant invention is to provide an effective prosthesis which can be comfortably worn on a male penis during sexual intercourse.

Other objects, features and advantages of the invention shall become apparent as the description thereof proceeds when considered in connection with the accompanying illustrative drawings.

DESCRIPTION OF THE DRAWING

In the drawing which illustrates the best mode presently contemplated for carrying out the present invention:

FIG. 1 is a perspective view of the prosthesis of the instant invention;

FIG. 2 is an elevational view thereof installed on a male;

FIG. 3 is a fragmentary perspective view of the end portion and the support wire elements with the end portion in an expanded disposition; and FIG. 4 is a similar view with the end portion in a closed disposition.

DESCRIPTION OF THE INVENTION

Referring now to the drawing, the prosthesis of the instant invention is illustrated in FIGS. 1–4 and generally indicated at 10 in FIGS. 1 and 2. The prosthesis 10 comprises a ring-like end portion 12, a pair of elongated support wire elements 14, a retaining ring 15, a pair of wire loops 16, a resilient band 18, and a stabilizer member 20. As illustrated in FIG. 2, the prosthesis 10 is adapted to be assembled on a penis 22 of a male 24 so that the end portion 12 substantially encircles the shaft 25 of the penis 22 adjacent the base of the glans 26 and so that the wire elements 14 pass along the underside of the penis 22 and along opposite sides of the scrotum 28 to points behind the scrotum 28. As further illustrated, when the prosthesis 10 is assembled on the penis 22, the wire loops 16 project downwardly from the support wire elements 14 behind the scrotum 28, and the resilient band 18 extends from the wire loops 16 over the upper side of the penis 22 adjacent the base thereof for urging the penis 22 forwardly and also slightly upwardly. The stabilizer member 20 extends rearwardly and upwardly from the wire loops 16 in the posterior crevice between the buttocks for providing increased stability for the prosthesis 10.

The end portion 12 is of open ring-like configuration, and it is dimensioned to be received on the shaft 25 of the penis 22 adjacent the base of the glans 26 so that it extends substantially therearound. The end portion 12 includes first and second ends 30 and 32, respectively, which are separable for increasing the diameter of the end portion 12 to enable it to be more easily assembled onto and removed from the penis 22. The end portion 12 comprises a center ring-like wire element 34 and a cushioned outer casing 36 which is preferably made from a suitable cushioned plastic material and coextends with the ring-like wire element 34. The ring-like wire element 34 is preferably made from a suitable substantially rigid wire, such as a polished surgical stainless steel wire having a diameter of between approximately 0.040 and 0.060 inches and preferably having a diameter of approximately 0.050 inches.

The support wire elements 14 extend integrally from the ring-like wire element 34 at the opposite ends 30 and 32 of the end portion 12 so that the support wire elements 14 extend rearwardly from the end portion 12 along the underside of the shaft 25 of the penis 22 when the end portion 12 is assembled on the penis 22. The support wire elements 14 are preferably made from a suitable polished surgical stainless steel, and they preferably have diameters of between 0.040 and 0.060 inches to provide a desired level of rigidity therein. The support wire elements 14 are formed with inwardly converging bends 38 therein adjacent the end portion 12, and they are dimensioned so that they extend rearwardly to points behind the scrotum 28 when the end portion 12 is assembled on the penis 22. In this connection, when the prosthesis 10 is assembled on the penis 22, the rearward portions of the support wire elements 14 are normally disposed in slightly spaced relation to accommodate the scrotum 28 therebetween as the wire elements 14 pass on opposite sides of the scrotum 28.

The retaining ring 15 is preferably made from a relatively soft plastic material, and it is slidably received on the support wire elements 14. The retaining ring 15 is dimensioned to be received in the bends 38 for retaining the end portion 12 in a closed position wherein the first and second ends 30 and 32 are disposed in closely adjacent relation on the underside of the penis 22, and wherein the end portion 12 snugly engages the shaft 25 of the penis 22 adjacent the glans 26. The retaining ring 15 is, however, rearwardly slidable on the wire elements 14 to enable the end portion 12 to be moved to an expanded disposition for assembling it onto or removing it from the penis 22.

The loops 16 are also integrally formed with the wire elements 14 preferably from a suitable surgical stainless steel, and they extend downwardly from the rear ends of the wire elements 14 behind the scrotum 28 as illustrated in FIGS. 1 and 2. The loops 16 are formed as a means for securing the band 18 to the rear ends of the wire elements 14 by hooking it over the loops 16 as illustrated in FIG. 2. It will be understood, however, that other embodiments of the prosthesis of the instant invention which include other means for securing the band 18 to the rear end portion of at least one of the support wire elements 14 are contemplated.

The band 18 comprises a resiliently expandable band, and it is dimensioned to be assembled in a resiliently expanded disposition wherein it extends around the loops 16 and over the upper side of the penis 22 adjacent the base thereof as illustrated in FIG. 2. In this regard, the band 18 is dimensioned so that when it is assembled on the penis 22 in this manner, it resiliently urges the wire elements 14 forwardly and also upwardly slightly to thereby urge the penis 22 forwardly and also upwardly slightly to maintain the penis 22 in a natural erected disposition.

The stabilizer member 20 extends rearwardly from the loop elements 16 so that, in effect, it is attached to the support wire elements 14 through the loop elements 16, and it comprises a pair of stabilizer wires 40 which integrally extend rearwardly and upwardly from the loop elements 16 and an outer casing 42 which is preferably made from a suitable cushioned plastic material. The stabilizer member 20 is dimensioned so that it is receivable in the posterior cavity between the buttocks of the male 24 when the end portion 12, the support wire elements 14 and the band 18 are assembled on the penis 22. In this regard, the stabilizer member 20 is preferably dimensioned so that it extends along substantially the entire extent of the posterior crevice between the buttocks to a point adjacent the upper end of the crevice for providing increased stability in the prosthesis 10 when it is assembled on the penis 22 in the manner illustrated in FIG. 2.

For use and operation of the prosthesis 10, the end portion 12 is assembled on the shaft 25 of the penis 22 adjacent the base of the glans 26, the scrotum 28 is passed downwardly between the support wire elements 14, and the stabilizer member 20 is assembled in the posterior cavity between the buttocks. The retaining ring 15 is then advanced forwardly on the support wire elements 14 so that it is received in the bends 38 therein to retain the end portion 12 in snug engagement with the penis 22. The band 18 is then positioned so that it is hooked behind the loops 16 and extends over the upper side of the penis 22 adjacent the base thereof. When the prosthesis 10 is assembled on the penis 22 in this manner, the band 22 operates to urge the support wire elements 14 and the end portion 12 forwardly and also slightly upwardly to urge the penis 22 forwardly and also slightly upwardly. The stabilizer member 20 provides increased stability for the prosthesis 10, and the retaining ring 15 positively secures the end portion 12 on the penis 22. Accordingly, the penis 22 is effectively and comfortably retained in an erected position wherein it has a natural degree of stability and rigidity to enable the male 24 to effectively perform sexual intercourse.

It is seen, therefore, that the instant invention provides a highly effective prosthesis for assisting an impotent male to perform sexual intercourse. The prosthesis 10 can be effectively assembled on the penis 22 to provide a natural degree of rigidity and stability. Further, the prosthesis 10 can be worn by the male 24 without a significant degree of discomfort. As a result, the prosthesis 10 effectively enables the male 24 to perform sexual intercourse in a highly effective and natural manner. Accordingly, it is seen that the prosthesis of the instant invention represents a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A prosthesis for use by a human male for supporting the penis in an erected disposition during sexual intercourse comprising an open ring-like end portion having opposite first and second ends, said end portion being expandable by separating said first and second ends and being receivable in snug engagement on the shaft of said penis so that it extends substantially therearound adjacent the base of the glans with said first and second ends disposed in closely adjacent relation on the underside of said penis, a pair of elongated, substantially rigid support wire elements, said support wire elements extending rearwardly from said first and second ends in closely adjacent relation along the underside of the shaft of said penis and rearwardly along opposite sides of the scrotum to points therebehind when said end portion is assembled on said penis, a resilient band and means for securing said band to said wire elements at a point behind said scrotum, said band being receivable on said penis in a resiliently expanded disposition so that it extends forwardly from said securing means and across the upper side of said penis adjacent the base thereof and being operable through said wire elements and said end portion for resiliently urging said penis forwardly to maintain it in said erected disposition.

2. In the prosthesis of claim 1, said end portion comprising a substantially ring-like wire element, said ring-like wire element being integrally formed with said support wire elements.

3. In the prosthesis of claim 2, said end portion further comprising a cushioned outer casing over said ring-like wire element.

4. In the prosthesis of claim 1, said securing means comprising a pair of wire loops integrally formed with said support wire elements behind said scrotum.

5. The prosthesis of claim 1 further comprising a retainer ring slidably received on said support wire elements, said retainer ring being receivable on said support wire elements adjacent said end portion for drawing said first and second ends together to tighten said end portion around the shaft of said penis.

6. The prosthesis of claim 1 further comprising a stabilizer member connected to said support wire elements and extending rearwardly and upwardly in the posterior crevice between the buttocks for increasing the stability of said prosthesis.

7. In the prosthesis of claim 6, said securing means comprising a pair of wire loops integrally formed with said support wire elements behind said scrotum, said stabilizer member comprising a pair of stabilizer wire elements extending integrally rearwardly from said wire loops, said stabilizer member being connected to said support wire elements through said wire loops.

8. In the prosthesis of claim 7, said stabilizer member further comprising a cushioned outer casing on said stabilizer wire elements.

* * * * *